(12) United States Patent
Suzuki et al.

(10) Patent No.: US 7,872,148 B2
(45) Date of Patent: Jan. 18, 2011

(54) CAGE-SHAPED CYCLOBUTANOIC DIANHYDRIDES AND PROCESS FOR PRODUCTION THEREOF

(75) Inventors: Hideo Suzuki, Funabashi (JP); Takayuki Tamura, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 803 days.

(21) Appl. No.: 11/665,024

(22) PCT Filed: Oct. 18, 2005

(86) PCT No.: PCT/JP2005/019071

§ 371 (c)(1), (2), (4) Date: Apr. 10, 2007

(87) PCT Pub. No.: WO2006/043519

PCT Pub. Date: Apr. 27, 2006

(65) Prior Publication Data

US 2009/0012318 A1 Jan. 8, 2009

(30) Foreign Application Priority Data

Oct. 20, 2004 (JP) ............................. 2004-305384
Nov. 2, 2004 (JP) ............................. 2004-319740
Mar. 24, 2005 (JP) ............................. 2005-085162

(51) Int. Cl.
*C07D 493/08* (2006.01)
(52) U.S. Cl. .................................... 549/232
(58) Field of Classification Search ................. 549/235, 549/232
See application file for complete search history.

(56) References Cited

U.S. PATENT DOCUMENTS 3,139,395 A 6/1964 Griffin et al.
4,454,310 A 6/1984 Oka et al.

FOREIGN PATENT DOCUMENTS

EP 0 082 724 A1 6/1983
JP 58-208322 A 12/1983
JP 60-188427 A 9/1985
JP 2003-73338 A 3/2003

OTHER PUBLICATIONS

Griffin, G.W. et al., J. Am. Chem. Soc., 1961, vol. 83, pp. 2725-2728, Chemical Abstracts, 1961, vol. 55, col. 22159f-22160c.
Griffin G.W. et al., Rev. Chim., Acad. Rep. Populaire Roumaine, 1962, vol. 7, No. 2, pp. 901 to 906, Chemcial Abstracts, 1964, vol. 61, col. 4233e-4264b.

(Continued)

Primary Examiner—Bernard Dentz

(74) *Attorney, Agent, or Firm*—Birch, Stewart, Kolasch & Birch, LLP.

(57) ABSTRACT

A process which comprises reacting a 1,2,3,4-cyclobutane-tetracarboxylic-1,2:3,4-dianhydride [1] with an alcohol [2] in the presence of an acid catalyst to obtain a compound [3], isomerizing the compound [3] with a base catalyst into a compound [4], reacting the compound [4] with an organic acid to obtain a compound [5], and reacting the compound [5] with a dehydrating agent to obtain a 1,2,3,4-cyclobutanetetracarboxylic-1,3:2,4-dianhydride: wherein $R^1$ and $R^2$ are each independently hydrogen, halogeno, alkyl of 1 to 10 carbon atoms, halogenated alkyl of 1 to 10 carbon atoms, cycloalkyl of 3 to 8 carbon atoms, phenyl, or cyano; and $R^3$ is alkyl of 1 to 10 carbon atoms.

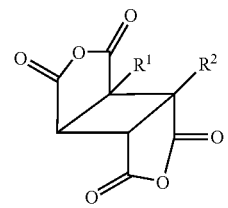

[1]

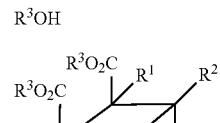

[2] $R^3OH$

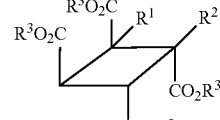

[3]

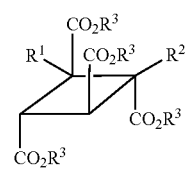

[4]

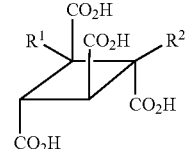

[5]

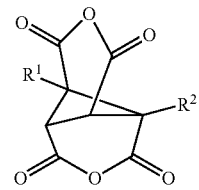

[6]

5 Claims, 3 Drawing Sheets

OTHER PUBLICATIONS

Maier, G. et al., Chemische Berichte, 1993, vol. 126, No. 8, pp. 1827-1833, Chemical Abstracts, 1994, vol. 120, abstract No. 216747.

Griffin G. W. et al., J. Am. Chem. Soc. 83, vol. 83, Jun. 20, 1961, pp. 2725-2728.

L.I. Peterson et al., The Journal of Organic Chemistry, vol. 33, No. 3, (1968), pp. 1018-1021.

Hinshaw, "Attempted Synthesis of cis-Cyclobutene-3,4-dicarboxaldehyde," J. Org. Chem., vol. 39, No. 26, pp. 3951-3953, Dec. 26, 1974, XP-002540815.

Jakovac et al., "Enzymes in Organic Sysnthesis. 24.[1] Preparations of Enantiomerically Pure Chiral Lactones via Stereospecific Horse Liver Alcohol Dehydrogenase Catalyzed Oxidations of Monocyclic Meso Diols[2]," J. Am. Chem. Soc., vol. 104, No. 17, Aug. 1982, pp. 4659-4665, XP-002540816.

Schenck et al., "Vierringsynthesen durch photosensibilisierte symmetrische und gemischte Cyclo-Addition," Chemische Berichte, vol. 95, No. 7, Dec. 23, 1961, pp. 1642-1647, XP-002540008.

Search Report mailed Sep. 14, 2009 in connection with European Application No. 05795540.3.

CAGE-SHAPED CYCLOBUTANOIC DIANHYDRIDES AND PROCESS FOR PRODUCTION THEREOF

TECHNICAL FIELD

The present invention relates to a cage-shaped cyclobutanoic dianhydride and a process for production thereof, said compound being for example a monomer of polyimide for optical use.

BACKGROUND ART

Polyimide resins generally find use in the electronic industry as an insulating material and a protective material for semiconductor devices and liquid crystal display devices because of their outstanding characteristic properties, such as high mechanical strength, high heat resistance, good electrical insulation, and good solvent resistance. Their recent prospective application area is optical communications, particularly optical waveguide.

The rapid development in this area needs materials with much more improved properties than before. Such materials must have not only good heat and solvent resistance but also various properties suitable for specific uses.

Among important properties is high transparency. High transparency is realized with a polyimide which is produced by polycondensation reaction between an alicyclic tetracarboxylic dianhydride and an aromatic diamine and ensuing imidization of the resulting polyimide precursor. The thus obtained polyimide has been reported to have high transparency with a comparatively low level of discoloration. (See Patent Documents 1 and 2.)

An example of the alicyclic tetracarboxylic dianhydride is 1,2,3,4-cyclobutanetetracarbocylic acid-1,3:2,4-dianhydride. It can be synthesized by combination of the following two schemes.

Synthesis from dimethyl fumarate (A) into trans, trans, trans-1,2,3,4-cyclobutanetetracarboxylic acid (D). (See Non-Patent Document 1.)

Synthesis from trans, trans, trans-1,2,3,4-cyclobutanetetracarboxylic acid (D) into 1,2,3,4-cyclobutanetetracarboxylic acid-1,3:2,4-dianhydride (E). (See Non-Patent Document 2.)

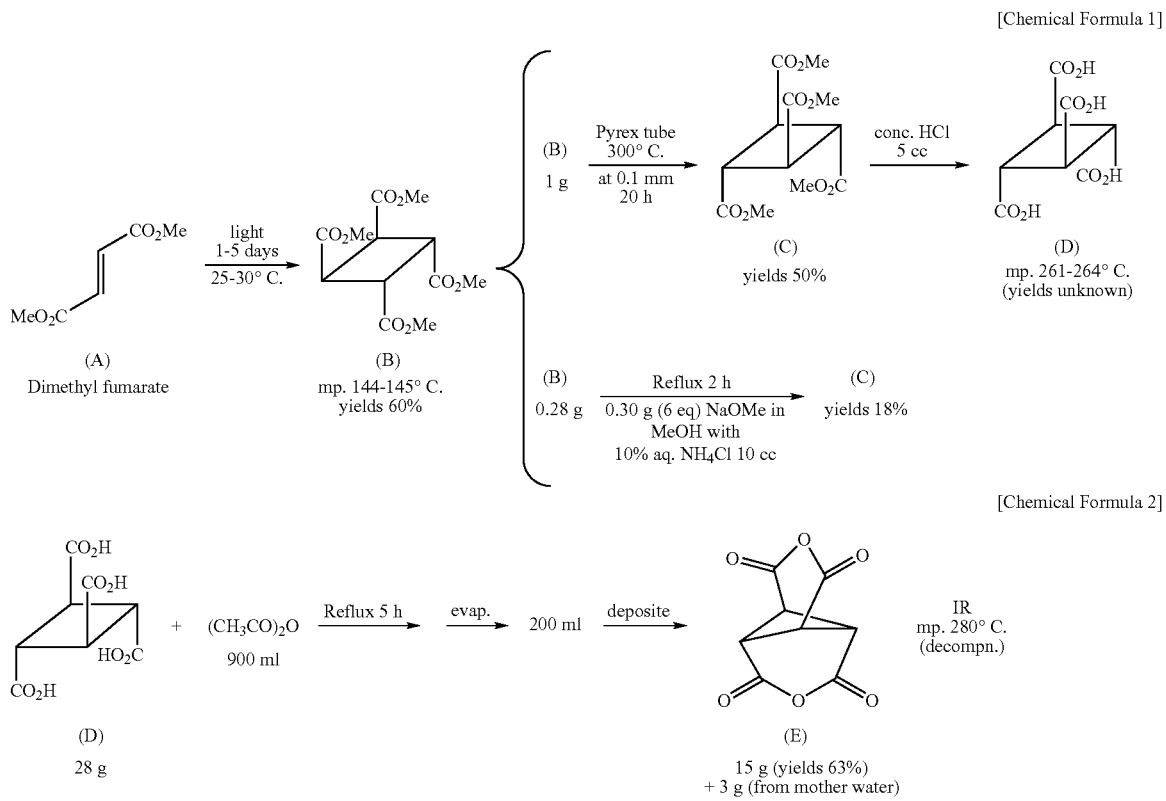

[Chemical Formula 1]

[Chemical Formula 2]

The process disclosed in Non-Patent Document 1 suffers the following disadvantages.
(1) The first step (for photoreaction) takes a very long time (one to five days).
(2) The second step (for isomerization) needs a high temperature (300° C.).
(3) The alternative second step (for isomerization) needs a large amount of base (6 equivalents) and is very poor in yields.
(4) The third step (for hydrolysis) needs concentrated hydrochloric acid, with nothing disclosed about yields.

The process disclosed in Non-Patent Document 2 suffers the disadvantage of precipitating 1,2,3,4-cyclobutanetetracarboxylic acid-1,3:2,4-dianhydride, which is the object product (E), in the form of colored solid. Moreover, it is unclear whether the disclosed process actually gives the cyclic compound as desired because the object product was examined for chemical structure only by IR but not by single-crystal X-ray diffractometry (for absolute structure).

In addition, there is no known compound composed of 1,2,3,4-cyclobutanetetracarboxylic acid-1,3:2,4-dianhydride and alkyl groups attached to the cyclobutane ring.

Patent Document 1:
JP-A 60-188427
Patent Document 2:
JP-A 58-208322
Non-Patent Document 1:
J. Am. Chem. Soc., 83, 2725-8 (1961), vol. 83, pp. 2725-2728.
Non-Patent Document 2:
J. Org. Chem., 33(3), 1018-1021 (1968).

DISCLOSURE OF INVENTION

Problems to be Solved by the Invention

It is an object of the present invention, which was completed in view of the foregoing, to provide a cage-shaped cyclobutanoic dianhydride and a process for production thereof, said compound being a monomer of polyimide for optical use. The polyimide has high optical transparency and improved heat resistance and is suitable for liquid crystal alignment layers and optical waveguides for optical communications.

Means for solving the problems

The present invention is based on an idea that polyimide will improve in transparency and heat resistance if it has a higher degree of polymerization and a higher linearity of main chain and that such an improved polyimide will result from a symmetric cage-shaped cyclobutanoic dianhydride as its monomer, which is typified by 1,2,3,4-cyclobutanetetracarboxylic acid-1,3:2,4-dianhydride. In fact, this monomer gave a polyimide which exhibited good main chain linearity, high degree of polymerization, high heat resistance, and increased solubility in organic solvents upon introduction of alkyl groups. The present inventors established a practical process for producing 1,2,3,4-cyclobutanetetracarboxylic acid-1,3:2,4-dianhydride from 1,2,3,4-cyclobutanetetracarboxylic acid-1,2:3,4-dianhydride.

Accordingly, the invention provides the following cage-shaped cyclobutanoic dianhydrides and process for production thereof (1) to (46).

(1) A process which includes reacting 1,2,3,4-cyclobutanetetracarboxylic acid-1,2:3,4-dianhydride represented by the formula [1]

[Chemical Formula 3]

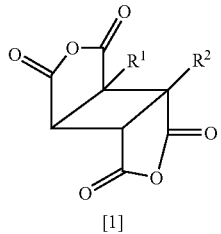

(where $R^1$ and $R^2$ each independently denotes a hydrogen atom, halogen atom, $C_{1-10}$ alkyl group, $C_{1-10}$ halogenated alkyl group, $C_{3-8}$ cycloalkyl group, phenyl group, or cyano group) with an alcohol represented by the formula [2]

[Chemical Formula 4]

$$R^3OH \qquad [2]$$

(where $R^3$ denotes a $C_{1-10}$ alkyl group)

in the presence of an acid catalyst, thereby producing cis, trans, cis-1,2,3,4-cyclobutanetetracarboxylic acid tetraester represented by the formula [3]

[Chemical Formula 5]

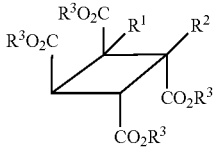

(where $R^1$, $R^2$, and $R^3$ are defined as above.)

(2) The process for producing cis, trans, cis-1,2,3,4-cyclobutanetetracarboxylic acid tetraester as defined in (1) above in which the acid catalyst is sulfuric acid.

(3) A process which includes isomerizing cis, trans, cis-1,2,3,4-cyclobutanetetracarboxylic acid tetraester represented by the formula [3] with the help of a base catalyst,

[Chemical Formula 6]

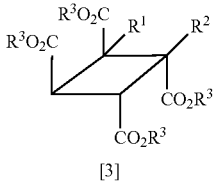

(where $R^1$, $R^2$, and $R^3$ are defined as above)

thereby producing trans, trans, trans-1,2,3,4-cyclobutanetetracarboxylic acid tetraester represented by the formula [4]

[Chemical Formula 7]

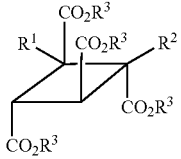

(where $R^1$, $R^2$, and $R^3$ are defined as above.)

(4) The process for producing trans, trans, trans-1,2,3,4-cyclobutanetetracarboxylic acid tetraester as defined in (3) above in which the base catalyst is metal alcoholate.

(5) The process for producing trans, trans, trans-1,2,3,4-cyclobutanetetracarboxylic acid tetraester as defined in (3) above in which the base catalyst is potassium t-butoxide.

(6) The process for producing trans, trans, trans-1,2,3,4-cyclobutanetetracarboxylic acid tetraester as defined in (3) above in which isomerization is carried out at −100° C. to 200° C.

(7) The process for producing trans, trans, trans-1,2,3,4-cyclobutanetetracarboxylic acid tetraester as defined in (3) above in which isomerization is carried out in an ether solvent.

(8) A process which includes reacting trans, trans, trans-1,2,3,4-cyclobutanetetracarboxylic acid tetraester represented by the formula [4]

[Chemical Formula 8]

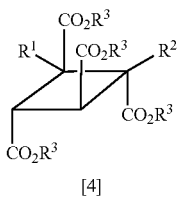

[4]

(where $R^1$, $R^2$, and $R^3$ are defined as above)

with an organic acid, thereby producing trans, trans, trans-1,2,3,4-cyclobutanetetracarboxylic acid represented by the formula [5]

[Chemical Formula 9]

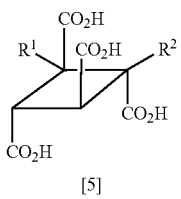

[5]

(where $R^1$ and $R^2$ are defined as above.)

(9) The process for producing trans, trans, trans-1,2,3,4-cyclobutanetetracarboxylic acid as defined in (8) above in which the organic acid is formic acid.

(10) The process for producing trans, trans, trans-1,2,3,4-cyclobutanetetracarboxylic acid as defined in (8) above in which the organic acid is formic acid and p-toluenesulfonic acid.

(11) The process for producing trans, trans, trans-1,2,3,4-cyclobutanetetracarboxylic acid as defined in (8) above in which the reaction is carried out at 0° C. to 200° C.

(12) A process which includes reacting trans, trans, trans-1,2,3,4-cyclobutanetetracarboxylic acid represented by the formula [5]

[Chemical Formula 10]

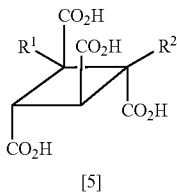

[5]

(where $R^1$, $R^2$, and $R^3$ are defined as above.)

with a dehydrating agent, thereby producing 1,2,3,4-cyclobutanetetracarboxylic acid-1,3:2,4-dianhydride represented by the formula [6]

[Chemical Formula 11]

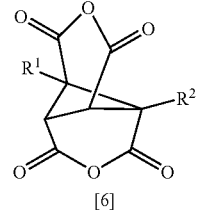

[6]

(where $R^1$ and $R^2$ are defined as above.)

(13) The process for producing 1,2,3,4-cyclobutanetetracarboxylic acid-1,3:2,4-dianhydride as defined in (12) above in which the dehydrating agent is an organic acid anhydride.

(14) The process for producing 1,2,3,4-cyclobutanetetracarboxylic acid-1,3:2,4-dianhydride as defined in (12) above in which the reaction is carried out in an aromatic hydrocarbon solvent.

(15) A process which includes reacting 1,2,3,4-cyclobutanetetracarboxylic acid-1,2:3,4-dianhydride represented by the formula [1]

[Chemical Formula 12]

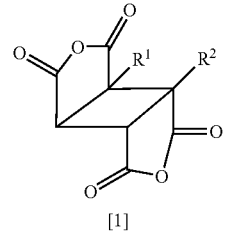

[1]

(where $R^1$ and $R^2$ are defined as above)

with a dialkyl sulfate represented by the formula [7]
[Chemical Formula 13]

$$R^3{}_2SO_4 \qquad [7]$$

(where $R^3$ is defined as above)

in the presence of a base catalyst, thereby producing cis, trans, cis-1,2,3,4-cyclobutanetetracarboxylic acid tetraester represented by the formula [3]

[Chemical Formula 14]

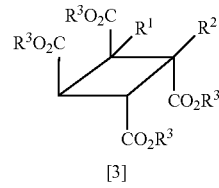

[3]

(where $R^1$, $R^2$, and $R^3$ are defined as above.)

(16) The process for producing cis, trans, cis-1,2,3,4-cyclobutanetetracarboxylic acid tetraester as defined in (15) above in which the dialkyl sulfate represented by the formula [7] is dimethyl sulfate.

(17) The process for producing cis, trans, cis-1,2,3,4-cyclobutanetetracarboxylic acid tetraester as defined in (15) above in which the base catalyst is an aliphatic amine.

(18) A process which includes reacting trans, trans, trans-1,2,3,4-cyclobutanetetracarboxylic acid tetraester represented by the formula [4]

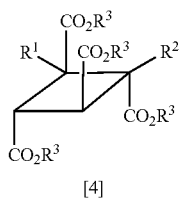

[Chemical Formula 15]

[4]

(where $R^1$, $R^2$, and $R^3$ are defined as above)

with an inorganic acid, thereby producing trans, trans, trans-1,2,3,4-cyclobutanetetracarboxylic acid represented by the formula [5]

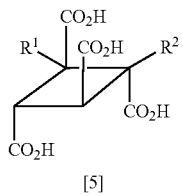

[Chemical Formula 16]

[5]

(where $R^1$ and $R^2$ are defined as above.)

(19) The process for producing trans, trans, trans-1,2,3,4-cyclobutanetetracarboxylic acid as defined in (18) above in which the inorganic acid is hydrochloric acid.

(20) The process for producing trans, trans, trans-1,2,3,4-cyclobutanetetracarboxylic acid as defined in (18) above in which the reaction is carried out while alcohol as a by-product is being distilled away from the reaction vessel.

(21) A process which includes converting the compound of the formula [3] obtained by the process of (1) into the compound of the formula [4] obtained by the process of (3), converting the compound of the formula [4] into the compound of the formula [5] by the process of (8), and converting the compound of the formula [5] into the compound of the formula [6] by the process of (12), thereby producing 1,2,3,4-cyclobutanetetracarboxylic acid-1,3:2,4-dianhydride.

(22) A process which includes converting the compound of the formula [3] obtained by the process of (15) into the compound of the formula [4] obtained by the process of (3), converting the compound of the formula [4] into the compound of the formula [5] by the process of (18), and converting the compound of the formula [5] into the compound of the formula [6] by the process of (12), thereby producing 1,2,3,4-cyclobutanetetracarboxylic acid-1,3:2,4-dianhydride.

(23) The process for producing cis, trans, cis-1,2,3,4-cyclobutanetetracarboxylic acid tetraester as defined in (1) or (2) above in which $R^1$ and $R^2$ are hydrogen atoms.

(24) The process for producing trans, trans, trans-1,2,3,4-cyclobutanetetracarboxylic acid tetraester as defined in any of (3) to (7) above in which $R^1$ and $R^2$ are hydrogen atoms.

(25) The process for producing trans, trans, trans-1,2,3,4-cyclobutanetetracarboxylic acid as defined in any of (8) to (11) above in which $R^1$ and $R^2$ are hydrogen atoms.

(26) The process for producing 1,2,3,4-cyclobutanetetracarboxylic acid-1,3:2,4-dianhydride as defined in any of (12) to (14) and (21) above in which $R^1$ and $R^2$ are hydrogen atoms.

(27) The process for producing cis, trans, cis-1,2,3,4-cyclobutanetetracarboxylic acid tetraester as defined in any of (15) to (17) above in which $R^1$ and $R^2$ are independently $C_{1-10}$ alkyl groups.

(28) The process for producing trans, trans, trans-1,2,3,4-cyclobutanetetracarboxylic acid tetraester as defined in any of (3) to (7) above in which $R^1$ and $R^2$ are independently $C_{1-10}$ alkyl groups.

(29) The process for producing trans, trans, trans-1,2,3,4-cyclobutanetetracarboxylic acid as defined in any of (18) to (20) above in which $R^1$ and $R^2$ are independently $C_{1-10}$ alkyl groups.

(30) The process for producing 1,2,3,4-cyclobutanetetracarboxylic acid-1,3:2,4-dianydride as defined in any of (12) to (14) and (22) above in which $R^1$ and $R^2$ are independently $C_{1-10}$ alkyl groups.

(31) The process for producing cis, trans, cis-1,2,3,4-cyclobutanetetracarboxylic acid tetraester as defined in any of (15) to (17) above in which $R^1$ and $R^2$ are methyl groups.

(32) The process for producing trans, trans, trans-1,2,3,4-cyclobutanetetracarboxylic acid tetraester as defined in any of (3) to (7) above in which $R^1$ and $R^2$ are methyl groups.

(33) The process for producing trans, trans, trans-1,2,3,4-cyclobutanetetracarboxylic acid as defined in any of (18) to (20) above in which $R^1$ and $R^2$ are methyl groups.

(34) The process for producing 1,2,3,4-cyclobutanetetracarboxylic acid-1,3:2,4-dianydride as defined in any of (12) to (14) and (22) above in which $R^1$ and $R^2$ are methyl groups.

(35) A 1,2,3,4-cyclobutanetetracarboxylic acid-1,3:2,4-dianydride represented by the formula [8]

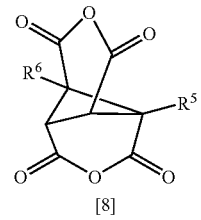

[Chemical Formula 17]

[8]

(where $R^5$ and $R^6$ independently denote a halogen atom, $C_{1-10}$ alkyl group, $C_{1-10}$ alkoxy group, $C_{1-10}$ halogenated alkyl group, $C_{3-8}$ cycloalkyl group, phenyl group, or cyano group.)

(36) The 1,2,3,4-cyclobutanetetracarboxylic acid-1,3:2,4-dianydride as defined in (35) above in which $R^5$ and $R^6$ independently denote a $C_{1-10}$ alkyl group.

(37) The 1,2,3,4-cyclobutanetetracarboxylic acid-1,3:2,4-dianydride as defined in (36) above in which $R^5$ and $R^6$ are methyl groups.

(38) A cis, trans, cis-1,2,3,4-cyclobutanetetracarboxylic acid tetraester represented by the formula [9]

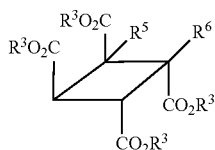

[Chemical Formula 18]

[9]

(where $R^3$, $R^5$, and $R^6$ are defined as above.)

(39) A cis, trans, cis-1,2,3,4-cyclobutanetetracarboxylic acid tetraester defined in (38) above in which $R^5$ and $R^6$ are independently $C_{1-10}$ alkyl groups.

(40) The cis, trans, cis-1,2,3,4-cyclobutanetetracarboxylic acid tetraester defined in (39) above in which $R^5$ and $R^6$ are methyl groups.

(41) A trans, trans, trans-1,2,3,4-cyclobutanetetracarboxylic acid tetraester represented by the formula [10]

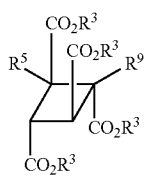

[Chemical Formula 19]

[10]

(where $R^3$, $R^5$, and $R^6$ are defined as above.)

(42) The trans, trans, trans-1,2,3,4-cyclobutanetetracarboxylic acid tetraester defined in (41) above in which $R^5$ and $R^6$ are independently $C_{1-10}$ alkyl groups.

(43) The trans, trans, trans-1,2,3,4-cyclobutanetetracarboxylic acid tetraester defined in (42) above in which $R^5$ and $R^6$ are methyl groups.

(44) A trans, trans, trans-1,2,3,4-cyclobutanetetracarboxylic acid represented by the formula [11]

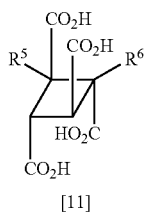

[Chemical Formula 20]

[11]

(where $R^5$ and $R^6$ are defined as above.)

(45) The trans, trans, trans-1,2,3,4-cyclobutanetetracarboxylic acid defined in (44) above in which $R^5$ and $R^6$ are independently $C_{1-10}$ alkyl groups.

(46) The trans, trans, trans-1,2,3,4-cyclobutanetetracarboxylic acid defined in (45) above in which $R^5$ and $R^6$ are methyl groups.

EFFECT OF THE INVENTION

The present invention provides a cage-shaped cyclobutanoic acid dianhydride and a process for production thereof, the compound being a monomer of polyimide for optical use. The polyimide has high optical transparency without absorption in UV region and improved heat resistance and hence is suitable for use as electronic material such as a protective material and insulating material for liquid crystal display devices and semiconductor devices and a raw material for waveguides in optical communications.

BEST MODE FOR CARRYING OUT THE INVENTION

Figure 1:
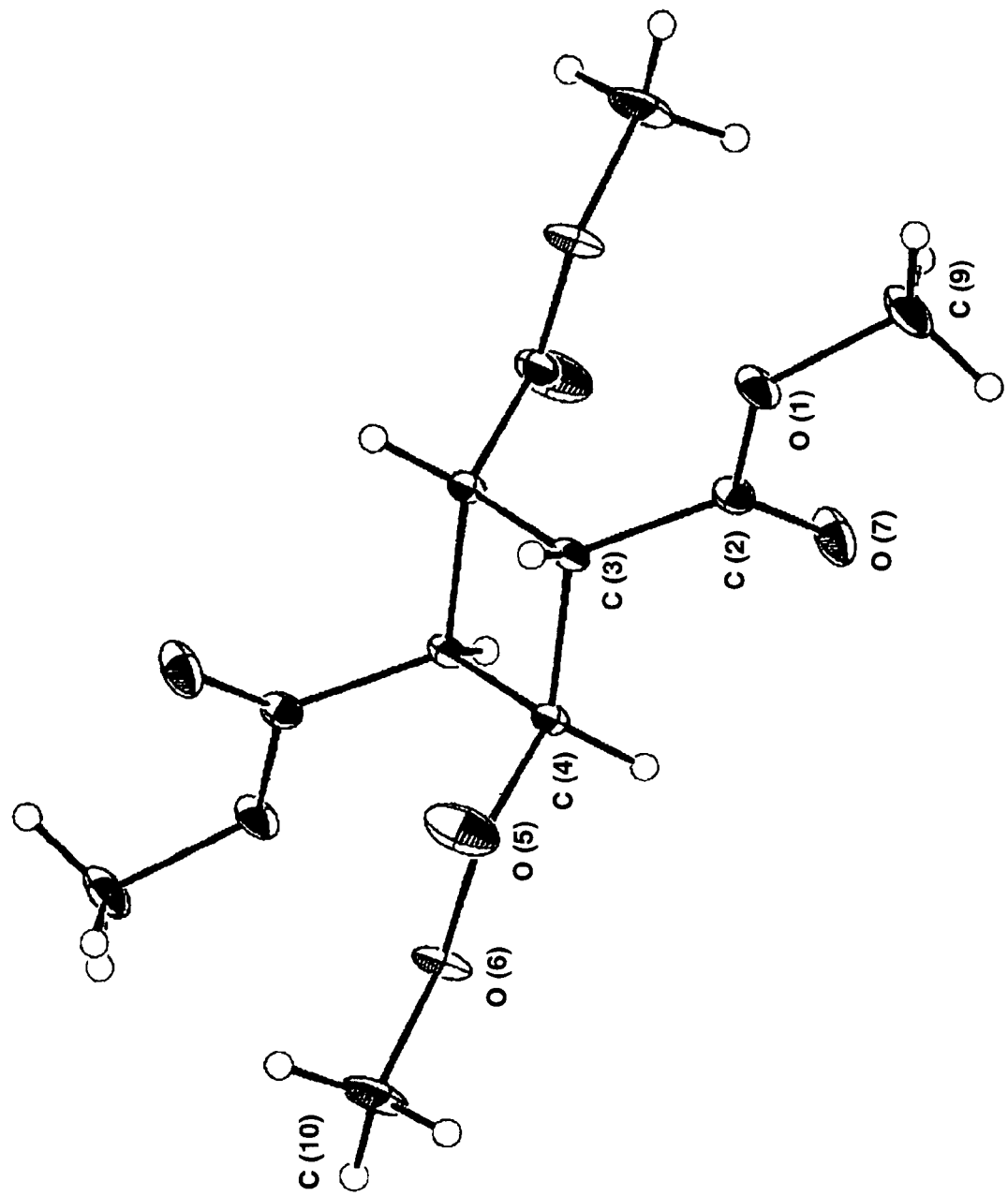
FIG. 1 is an X-ray diffraction chart of cis, trans, cis-tetramethyl-1,2,3,4-cyclobutanetetracarboxylate (in single-crystal form) which was obtained in Example 1.

The following is a detailed description of the present invention. Incidentally, those symbols "n", "i", "s", and "t" used hereunder stand for respectively normal, iso, secondary, and tertiary.

The 1,2,3,4-cyclobutanetetracarboxylic acid-1,3:2,4-dianhydride (abbreviated as cage-shaped CBDA compound hereinafter) represented by the formula [6] above is produced by the following process including first, second, third, and fourth steps. The first step and third step in the process may be replaced by first step (another one) and third step (another one), respectively.

Incidentally, the process should be performed in regular order from first step to fourth step.

[Chemical Formula 21]

First step

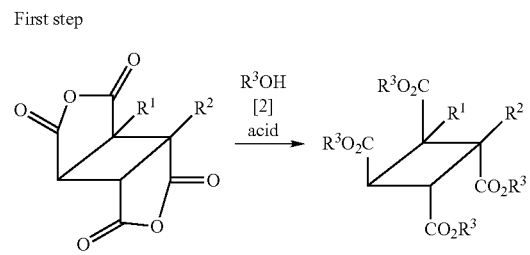

[1]  [3]

Second step

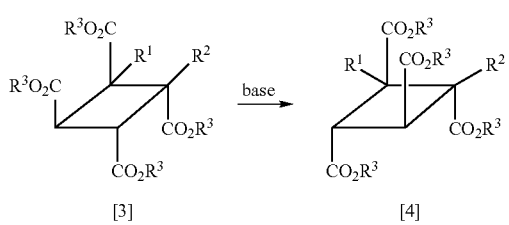

[3]  [4]

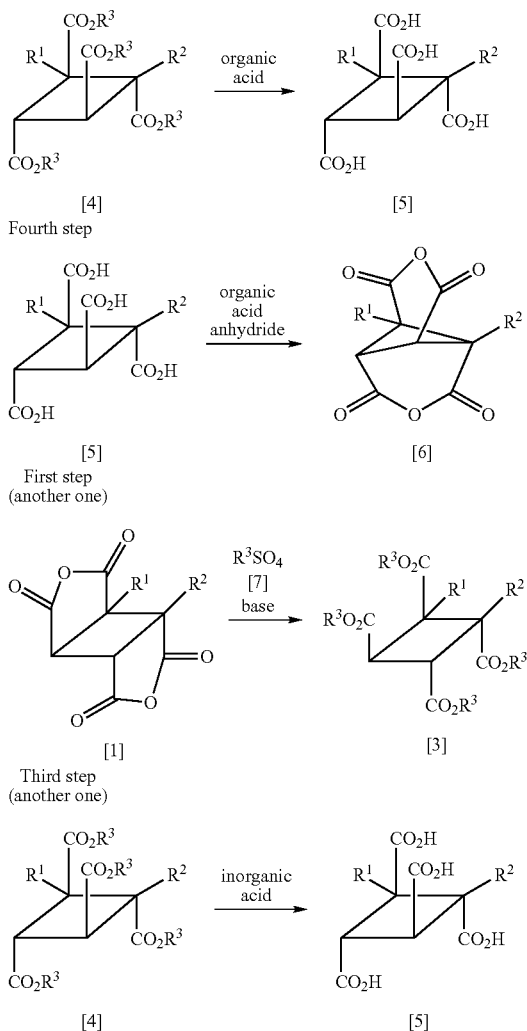

(where $R^1$ and $R^2$ each independently denotes a hydrogen atom, halogen atom, $C_{1-10}$ alkyl group, $C_{1-10}$ halogenated alkyl group, $C_{3-8}$ cycloalkyl group, phenyl group, or cyano group; and $R^3$ independently denotes a $C_{1-10}$ alkyl group.)

The atoms and groups represented by $R^1$ and $R^2$ are exemplified as follows.

The halogen atom includes a fluorine atom, chlorine atom, bromine atom, and iodine atom.

The $C_{1-10}$ alkyl group includes a methyl group, ethyl group, n-propyl group, i-propyl group, n-butyl group, i-butyl group, s-butyl group, t-butyl group, n-pentyl group, n-hexyl group, n-octyl group, and n-decyl group, which may be either straight or branched. Preferable among them are methyl group, ethyl group, n-propyl group, i-propyl group, n-butyl group, s-butyl group, t-butyl and n-pentyl group, which are $C_{1-5}$ alkyl groups. Of these examples, methyl group, ethyl group, and n-propyl group, which are $C_{1-3}$ groups, are desirable because of their limited steric hindrance.

The $C_{1-10}$ halogenated alkyl group includes a trifluoromethyl group, a pentafluoroethyl group, heptafluoropropyl group, perfluorooctyl group, and perfluorodecyl group. Of these examples, trifluoromethyl group, pentafluoroethyl group, and heptafluoropropyl group, which are $C_{1-3}$ halogenated alkyl groups, are desirable because of their limited steric hindrance.

The $C_{3-8}$ cycloalkyl group includes a cyclopropyl group, cyclobutyl group, cyclopentyl group, cyclohexyl group, cycloheptyl group, and cyclooctyl group. Of these examples, cyclopropyl group and cyclobutyl group, which are $C_{3-4}$ cycloalkyl groups, are desirable because of their small steric hindrance.

The groups represented by $R^3$ are exemplified as follows.

The $C_{1-10}$ alkyl group includes a methyl group, ethyl group, n-propyl group, i-propyl group, n-butyl group, i-butyl group, s-butyl group, t-butyl group, n-pentyl group, octyl group, and decyl group. Preferable among them are methyl group, ethyl group, n-propyl group, i-propyl group, n-butyl group, i-butyl group, s-butyl group, t-butyl group, and n-pentyl group, which are $C_{1-5}$ alkyl groups. Of these examples, methyl group, ethyl group, and n-propyl group, which are $C_{1-3}$ alkyl groups, are desirable because their small steric hindrance.

Each step in the process works in the following way.

[1] The First Step

This step is intended for reaction between 1,2,3,4-cyclobutanetetracarboxylic acid-1,2:3,4-dianhydride (abbreviated as CBDA compound hereinafter) and an alcohol represented by the formula [2] in the presence of an acid catalyst, to give a cis, trans, cis-1,2,3,4-cyclobutanetetracarboxylic acid tetraester (abbreviated as cis, trans, cis-TMCB compound hereinafter) represented by the formula [3].

The CBDA compound as a starting material represented by the formula [1] may be prepared from substituted maleic anhydride by photodimerization. A typical example of manufacturing process by photodimerization is disclosed in JP-A 59-212495.

The alcohol compound represented by the formula [2] includes those alcohols having a $C_{1-10}$ alkyl group such as methanol, ethanol, n-propanol, i-propanol, n-octanol, and n-decanol. Of these examples, methanol is desirable for economical reason.

The amount of the alcohol compound can be 4 to 100 times, preferably 10 to 50 times (in mol), the amount of the substrate.

The acid catalyst may be selected from inorganic acids, such as hydrochloric acid and sulfuric acid, and solid acids, such as heteropolyacid and cation-exchange resin. Preferable among them is sulfuric acid.

The amount of the acid catalyst can be 0.1 to 20 wt %, preferably 1 to 10 wt %, of the substrate.

The reaction should be carried out usually at a temperature near the boiling point of the alcohol. Thus the reaction temperature ranges from 20 to 200° C.; preferably 50 to 150° C.

The progress of the reaction can be followed by gas chromatography.

The reaction is completed by the procedure exemplified as follows. After the starting material has been consumed completely, the reaction product is cooled to room temperature and filtered off to collect crystals (in the case where the acid catalyst is sulfuric acid). The collected crystals are washed with the alcohol used for the reaction and then dried. In this way there is obtained the cis, trans, cis-TMCB compound as desired.

This step is useful particularly in the case where $R^1$ and $R^2$ are hydrogen atoms.

[2] The First Step (Another One)

This step is intended for reaction between a CBDA compound and a dialkyl sulfate represented by the formula [7] in the presence of a base catalyst, to give a cis, trans, cis-TMCB compound.

The dialkyl sulfate includes a $C_{1-10}$ dialkyl sulfate such as dimethyl sulfate, diethyl sulfate, di-n-propyl sulfate, di-i-propyl sulfate, di-n-butyl sulfate, di-1-butyl sulfate, di-s-butyl sulfate, di-n-amyl sulfate, di-n-hexyl sulfate, di-n-heptyl sulfate, di-n-octyl sulfate, di-n-nonyl sulfate, and di-n-decyl sulfate. Of these examples, dimethyl sulfate is desirable for economical reason.

The amount of the dialkyl sulfate can be 2 to 10 times, preferably 2 to 4 times (in mol), the amount of the substrate.

This step needs a base catalyst, which plays an important role. Examples of the base catalyst include alkylamines (such as diethylamine, triethylamine, diisopropylamine, and di-n-butylamine) and aromatic amines (such as pyridine and picoline). Preferable among them is diisopropylamine. The amount of the base catalyst can be 2 to 10 times, preferably 2 to 4 times (in mol), the amount of the substrate.

This step may or may not require any solvent. A preferred solvent is an alcohol compound which has the same alkyl group as the constituent of the dialkyl sulfate. For example, methanol matches dimethyl sulfate and ethanol matches diethyl sulfate. The amount of the alcohol can be 1 to 20 times, preferably 2 to 10 times (in weight), the amount of the substrate.

The reaction can be carried out usually at a temperature near the boiling point of the alcohol. Thus the reaction temperature ranges from 20 to 200° C., preferably 50 to 150° C.

The progress of the reaction can be followed by gas chromatography.

The reaction is completed by the procedure exemplified as follows. After the starting material has been consumed completely, the reaction product is concentrated and the resulting residues are dissolved in a mixture of toluene and dilute hydrochloric acid. The organic layer is washed with an aqueous solution of sodium bicarbonate and then with water to give the desired product in the form of crude crystals. The crude crystals are recrystallized from toluene solution and n-heptane solution. In this way there is obtained the cis, trans, cis-TMCB compound as desired.

This step is useful particularly in the case where $R^1$ and $R^2$ are independently $C_{1-10}$ alkyl groups, such as methyl group.

[3] The Second Step

This step is intended for isomerization of the cis, trans, cis-TMCB compound with the help of a base catalyst to give the trans, trans, trans-1,2,3,4-cyclobutanetetracarboxylic acid tetraester (abbreviated as all trans-TMCB compound hereinafter) represented by the formula [4].

The base catalyst may be selected from alcoholates, carbonates, hydroxides, and oxides of alkali metal or alkaline earth metal. The alkali metal is exemplified by lithium, sodium, and potassium, and the alkaline earth metal is exemplified by magnesium, calcium, and barium.

Preferable among these examples are such alcoholates as sodium methoxide, sodium ethoxide, sodium t-butoxide, potassium methoxide, potassium ethoxide, and potassium, t-butoxide. Sodium methoxide and potassium t-butoxide are more preferable, and potassium t-butoxide is most desirable.

The amount of the base catalyst can be 0.1 to 100 mol %, particularly 0.5 to 20 mol %, of the substrate.

This step employs a solvent selected from many varieties including ethers (such as tetrahydrofuran (THF), 1,4-dioxane, 1,2-dimethoxyethane, and diethyleneglycol dimethyl ether) and alcohols (such as methanol, ethanol, n-butanol, i-propanol, n-butanol, i-butanol, and s-butanol). Of these examples, ethers are preferable because of their ability to promote the reaction and their utility at low temperatures.

The amount of the solvent can be 1 to 50 times, particularly 2 to 10 times (in weight) of the substrate.

The reaction can be carried out usually at −100° C. to 200° C., preferably −50° C. to 100° C. A reaction temperature lower than 20° C. is acceptable for reactions in ether as the solvent.

The progress of the reaction can be followed by gas chromatography.

The treatment after the reaction includes, but not limited to the followings.

The reaction is usually followed by the post-treatment which consists of concentrating the reaction product, extracting the resulting residue with 1,2-dichloroethane (EDC) and water, separating the extract (acidified with 35% HCl) into an EDC layer and a water layer, concentrating the EDC layer to give white crystals, dissolving the white crystals in methanol, ice-cooling the methanol solution (slightly concentrated) for precipitation of crystals, collecting the crystals (by filtration), washing the collected crystals with methanol, and drying in vacuo the washed crystals. In this way there is obtained all trans-TMCB compound which gives a single peak in gas chromatography. This procedure is suitable in the case where $R^1$ and $R^2$ are hydrogen atoms.

The above-mentioned post-treatment may be modified such that the concentrated reaction product is extracted with toluene and water and the organic layer is separated and concentrated to give white crystals, which are subsequently recrystallized from toluene and n-heptane. In this way there is obtained all trans-TMCB compound which gives a single peak in gas chromatography. This step is useful in the case where $R^1$ and $R^2$ are independently $C_{1-10}$ alkyl groups, such as methyl group.

[4] The Third Step

This step is intended for reaction between the all trans-TMCB compound and an organic acid to give a trans, trans, trans-1,2,3,4-cyclobutanetetracarboxylic acid (abbreviated as all trans-CBTC compound) represented by the formula [5].

The organic acid may be selected from fatty acids (such as formic acid, acetic acid, and propionic acid) and sulfonic acid (such as methanesulfonic acid, ethanesulfonic acid, and trifluoromethanesulfonic acid). Of these examples, formic acid is preferable because of its ability to simplify the procedure of reaction.

The amount of the organic acid can be more than 4 mol equivalent than the amount of the substrate. Moreover, an excess amount from 10 to 100 mol equivalent is desirable because distilling the acid ester (occurring as a by-product) together with part of the organic acid promotes the reaction.

The reaction system for this step may optionally be incorporated with benzenesulfonic acid or p-toluenesulfonic acid, with the latter being preferable. Their amount can be 0.1 to 10 wt %, preferably 0.5 to 5 wt %, of the amount of the substrate.

The reaction solution gradually gives white crystals that separate out as it becomes concentrated, and their amount increases as the acid ester (occurring as a by-product) is distilled away until the starting material is completely consumed with $^1$H-NMR. After the starting material completely consumed, the reaction solution is cooled to room temperature and the precipitated crystals are filtered out. The collected crystals are washed with ethyl acetate and then dried in vacuo. In this way there is obtained the desired all trans-CBTC compound in the form of white crystals.

This step is useful in the case where $R^1$ and $R^2$ are hydrogen atoms.

The Third Step (Another One)

This step is intended for reaction between the all trans-TMCB compound and an inorganic acid to give the all trans-CBTC compound.

The inorganic acid may be selected from hydrochloric acid, hydrobromic acid, sulfuric acid, and phosphoric acid. Hydrochloric acid permits simple operation.

The amount of the inorganic acid can be more than 4 to 50 mol equivalent (in excess) of the amount of the substrate. This step can be carried out by distilling away the alcohol (occurring as a by-product) so as to promote the reaction.

The reaction temperature can be 50° C. to 200° C., preferably 60° C. to 150° C.

The reaction is continued with distillation until the starting material is completely consumed with $^1$H-NMR, and the remaining reaction solution is dehydrated to dryness by azeotropic distillation with toluene. The residues are recrystallized from ethyl acetate solution. In this way there is obtained the desired all trans-CBTC compound in the form of white crystals.

This step is useful in the case where $R^1$ and $R^2$ are independently $C_{1-10}$ alkyl groups (e.g., methyl groups).

[5] The Fourth Step

This process is intended for reaction between the all trans-CBTC compound and a dehydrating agent to produce the cage-shaped CBDA compound.

The dehydrating agent is selected from aliphatic carboxylic acid anhydride, 1,3-dicyclohexylcarbodiimide (DCC for short hereinafter), and 2-chloro-1,3-dimethylimidazolinium chloride (DMC for short hereinafter). Preferable among them are inexpensive aliphatic carboxylic acid anhydride, especially acetic anhydride.

The amount of the dehydrating agent can be 2 to 50 equivalent, preferably 2 to 10 equivalents, for the amount of the substrate.

This step may or may not require any organic solvent which is not directly involved in reaction. The dehydrating agent added in an excess amount may serve as the solvent. Examples of the organic solvent include aromatic hydrocarbons (such as toluene and xylene), halogenated hydrocarbons (such as 1,2-dichloroethane and 1,2-dichloropropane), and 1,4-dioxane. Preferable among them are aromatic hydrocarbons which give colorless cage-shaped CBDA compounds.

The amount of the solvent can be 1 to 20 times, preferably 1 to 10 times (in weight), the amount of the substrate.

The reaction temperature can be 50° C. to 200° C., preferably 60° C. to 150° C., which is close to the boiling point of the dehydrating agent or solvent.

The reaction time ranges from 1 to 20 hours, preferably from 2 to 10 hours, depending on the reaction temperature.

After the reaction is complete, the dehydrating agent (and the optional solvent) are distilled away. In this way there is obtained the desired cage-shaped CBDA compound (which has a practically high purity but may be recrystallized, if necessary).

The third and fourth steps mentioned above may be combined together in such a way that the reaction product from the third step (which employs formic acid) undergoes dehydration in the fourth step, and the formic acid and the acetic acid (as a by-product arising from acetic anhydride used as the dehydrating agent) are distilled away together with the optional organic solvent. This procedure gives the desired cage-shaped CBDA compound efficiently.

Incidentally, the reactions in the above-mentioned steps may be carried out continuously or batchwise and at atmospheric pressure or under pressure.

The present invention also provides 1,2,3,4-cyclobutanetetracarboxylic acid-1,3:2,4-dianhydride represented by the formula [8] below.

[Chemical Formula 22]

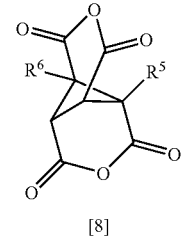

[8]

(where $R^5$ and $R^6$ independently denote a halogen atom, $C_{1-10}$ alkyl group, $C_{1-10}$ alkoxy group, $C_{1-10}$ halogenated alkyl group, $C_{3-8}$ cycloalkyl group, phenyl group, or cyano group.)

Typical examples of $R^5$ and $R^6$ include halogen atoms (such as fluorine atom, chlorine atom, bromine atom, and iodine atom), $C_{1-10}$ alkyl groups (such as methyl group, ethyl group, propyl group, octyl group, and decyl group), $C_{1-10}$ halogenated alkyl group (such as trifluoromethoxy group, pentafluoroethoxy group, heptafluoropropoxy group, perfluorooctyloxy group, and perfluorodecyloxy group), $C_{3-8}$ cycloalkyl group (such as cyclopropyl group, cyclobutyl group, cyclopentyl group, cyclohexyl group, cycloheptyl group, and cyclooctyl group), phenyl group, and cyano group.

The present invention also provides an intermediate of the compound represented by the formula [8]. The intermediate includes cis, trans, cis-1,2,3,4-cyclobutanetetracarboxylic acid tetraester represented by the formula [9], trans, trans, trans-1,2,3,4-cyclobutanetetracarboxylic acid tetraester represented by the formula [10], and trans, trans, trans-1,2,3,4-cyclobutanetetracarboxylic acid represented by the formula [11].

[Chemical Formula 23]

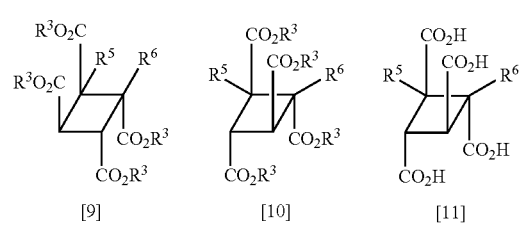

[9]   [10]   [11]

(where $R^3$, $R^5$, and $R^6$ are defined as above.)

Those compounds represented by the formulas [8] to in which $R^5$ and $R^6$ are $C_{1-10}$ alkyl groups may be produced from 1,2-dialkyl-1,2,3,4-cyclobutanetetracarboxylic acid-1,2:3,4-dianhydride, which is readily available.

For example, 1,4-dimethyl-1,2,3,4-cyclobutanetetracarboxylic acid-1,2:3,4-dianhydride can be produced by the method disclosed in JP-A 4-106127.

EXAMPLES

The invention will be described in more detail with reference to the following Examples, which are not intended to restrict the scope thereof. Reaction products were analyzed and identified by the methods specified below.

| [1] Gas chromatography (GC) | |
|---|---|
| Apparatus: | Shimadzu GC-17A, |
| Column: | capillary column CBP1-W25-100 (25 m × 0.53 mm$\phi$ × 1 μm) |
| Column temperature: | 100° C. (retained for 2 min) to 290° C. (retained for 10 min). |
| Rate of temperature increase: | 8° C./min |
| Inlet temperature: | 290° C. |
| Detector temperature: | 290° C. |
| Carrier gas: | helium |
| Detecting: | FID |
| [2] Mass spectroscopy (MASS) | |
| Apparatus: | LX-1000 (JEOL Ltd.) |
| Detecting method: | FAB |
| [3] $^1$H-NMR | |
| Apparatus: | ECP500 (JEOL) |
| Solvent: | DMSO-$d_6$ |
| [4] $^{13}$C-NMR | |
| Apparatus: | ECP500 (JEOL) |
| Solvent: | DMSO-$d_6$ |
| [5] Melting point (mp) | |
| Apparatus: | FP62 (Mettler Toledo) for automatic measurement |
| [6] [X-ray diffractometry] | |
| Apparatus: | DIP2030K (Mac Science) |
| X-ray: | Mo K$_\alpha$ (45 kV, 200 mA) |
| Performed at room temperature | |
| Specimen: | plate crystal (0.2 × 0.1 × 0.1 mm) |
| [7] [X-ray diffractometry] | |
| Apparatus: | DIP2030K (Mac Science) |
| X-ray: | Mo K$_\alpha$ (45 kV, 200 mA) |
| Performed at room temperature | |
| Specimen: | plate crystal (0.2 × 0.1 × 0.1 mm) |

Example 1

Synthesis of cis, trans, cis-tetramethyl-1,2,3,4-cyclobutane-tetracarboxylate

[Chemical Formula 24]

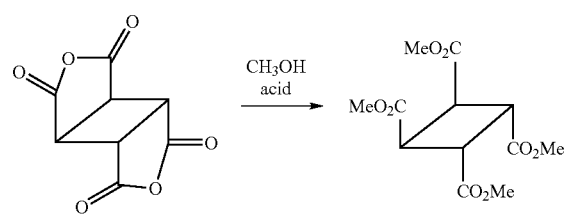

Synthesis started with charging a 200-mL four-neck flask of Pyrex (registered trade mark) glass with 1,2,3,4-cyclobutanetetracarboxylic acid-1,2,3,4-dianhydride (16.4 g or 83.6 mmol), 95% sulfuric acid (1.64 g), and methanol (98.4 g). The reactants underwent refluxing for 4 hours in an oil bath at 80° C. Crystals gradually separated out as refluxing proceeded.

The reaction was followed by cooling to room temperature and filtration for crystal collection. After washing with water and methanol and drying in vacuo, there was obtained 23.5 g of white crystals which gave a single peak in gas chromatography (GC). Yields: 97.5%.

This product was identified, by single-crystal X-ray diffractometry, as cis, trans, cis-tetramethyl-1,2,3,4-cyclobutanetetracarboxylate. This identification agreed with the following data of MASS, $^1$H-NMR, and $^{13}$C-NMR.

| MASS (FAB, m/e(%)): | 289 ([M + H]$^+$, 47), 257 (100), 154 (66) |
|---|---|
| $^1$H-NMR (DMSO-$d_6$, δ ppm): | 3.6778 (s, 4H), 3.6039 (s, 12H) |
| $^{13}$C-NMR (DMSO-$d_6$, δ ppm): | 40.0868, 52.1500, 170.8977 (each representing four carbons) |
| mp.: | 146.5 to 147.5° C. |

The result of the X-ray analysis of the single crystal of cis, trans, cis-tetramethyl-1,2,3,4-cyclobutanetetracarboxylate The X-ray analysis performed on the single crystal, which was obtained by natural concentration from a solution of cis, trans, cis-tetramethyl-1,2,3,4-cyclobutanetetracarboxylate dissolved in acetonitrile, gave the following results and the molecular structure as shown in FIG. 1.

| Molecular formula: | $C_{12}H_{16}O_8$ |
|---|---|
| Molecular weight: | 288.25 |
| Color and shape: | colorless and plate |
| Crystal system: | triclinic |
| Space group: | P-1 |
| Crystal form: | plane |
| Lattice constants: | a = 5.971(1) Å |
| | b = 6.461(1) Å |
| | c = 8.949(1) Å |
| | α = 98.534(8)° |
| | β = 101.277(6)° |
| | γ = 95.189(7)° |
| V = 332.29(8) Å$^3$ | |
| Z value = 1 | |
| Dx = 1.441 Mg/m$^3$ | |
| Mo K <α> radiation | |
| λ (MoKa) = 0.70926 Å, μ (MoKa) = 0.12 mm$^{-1}$ | |
| No. of measured reflections = 1414 | |
| No. of observed reflections = 1386 | |
| R(gt) = 0.09 | |
| wR(gt) = 0.37 | |
| Temp. = 298 K | |

Example 2

Synthesis of trans, trans, trans-tetramethyl-1,2,3,4-cyclobutanetetracarboxylate

[Chemical Formula 25]

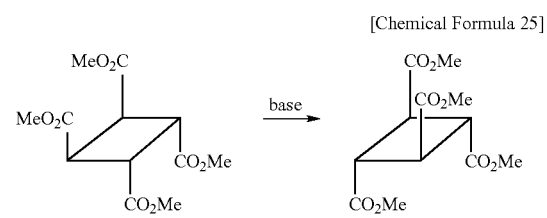

Synthesis started with charging a 100-mL four-neck flask of Pyrex (registered trade mark) glass with cis, trans, cis-tetramethyl-1,2,3,4-cyclobutanetetracarboxylate (2.88 g or 10.0 mmol), 95%-pure potassium t-butoxide (0.23 g or 20 mol %), and methanol (28.8 g). The reactants underwent refluxing for 8 hours in an oil bath at 80° C. The reaction was followed by concentration and extraction of residues with 1,2-dichloroethane (EDC) and water. With the extract acidified with 35% hydrochloric acid, the EDC layer was separated and analyzed by gas chromatography. There was obtained a chromatogram in which the reaction product accounts for 95% of the GC area.

Upon concentration, the separated EDC layer gave white crystals (2.7 g). The white crystals were purified by dissolution in methanol, concentration, and crystallization by ice-cooling. After washing with methanol and drying in vacuo, there was obtained 2.0 g of white crystals which gave a single peak in gas chromatography (GC).

This product was identified, by MASS, $^1$H-NMR, and $^{13}$C-NMR, as trans, trans, trans-tetramethyl-1,2,3,4-cyclobutanetetracarboxylate.

| MASS (FAB, m/e(%)): | 289 ([M + H]$^+$, 100), 257 (92), 154 (92) |
| --- | --- |
| $^1$H-NMR (DMSO-d$_6$, δ ppm): | 3.4217 (s, 4H), 3.6428 (s, 12H) |
| $^{13}$C-NMR (DMSO-d$_6$, δ ppm): | 39.3470, 52.2496, 171.0202 (each representing four carbons) |
| mp.: | 127.5 to 128.0° C. |

Examples 3 to 6

Synthesis of trans, trans, trans-tetramethyl-1,2,3,4-cyclobutanetetracarboxylate

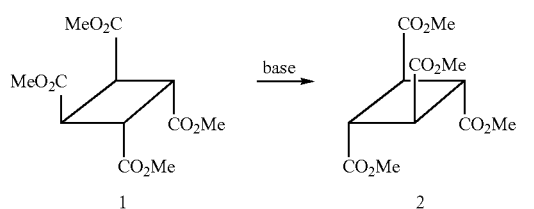

[Chemical Formula 26]

Synthesis started with charging a 50-mL four-neck flask of Pyrex (registered trade mark) glass with cis, trans, cis-tetramethyl-1,2,3,4-cyclobutanetetracarboxylate (0.864 g or 3.0 mmol), methanol (14.4 g), and any one of the bases shown in Table 1 below. The reaction was carried out in the same way as in Example 2 except that the reaction temperature and reaction time were changed as shown in Table 1 below. The reaction liquid was analyzed by gas chromatography to give the results shown in Table 1.

TABLE 1

| Example | Base | mg | (mol %) | Temp., ° C. | Time, h | GC area % 2 | GC area % 1 |
| --- | --- | --- | --- | --- | --- | --- | --- |
| 3 | t-BuOK | 69 | (20) | 63 | 1 | 86.0 | 12.9 |
| 4 | t-BuOK | 69 | (20) | 45 | 1 | 81.9 | 18.1 |
| 5 | t-BuOK | 29 | (5) | 63 | 2 | 80.2 | 16.9 |
| 6 | MeONa | 34 | (20) | 63 | 2 | 74.7 | 25.3 |

Example 7

Synthesis of trans, trans, trans-tetramethyl-1,2,3,4-cyclobutanetetracarboxylate Synthesis started with charging a 300-mL four-neck flask of Pyrex (registered trade mark) glass with cis, trans, cis-tetramethyl-1,2,3,4-cyclobutanetetracarboxylate (35 g or 121.4 mmol), 95%-pure potassium t-butoxide (2.72 g or 20 mol %), and methanol (175 g). The reactants underwent refluxing for 2 hours at 62° C. The reaction was followed by cooling to 52° C. and crystallization by addition of a seed crystal of all trans-TMCB. The reaction product containing white crystals was stirred for 2 hours each at 52° C., 40° C., and 25 to 30° C. The crystals were filtered out, washed with methanol, and dried in vacuo. Thus there was obtained the desired product (26.9 g) in the form of white crystals which gave a single peak in gas chromatography (GC). Yields: 76.9%.

This product was identified, by MASS, $^1$H-NMR, and $^{13}$C-NMR, as trans, trans, trans-tetramethyl-1,2,3,4-cyclobutanetetracarboxylate.

Example 8

Synthesis of trans, trans, trans-1,2,3,4-cyclobutanetetracarboxylic acid

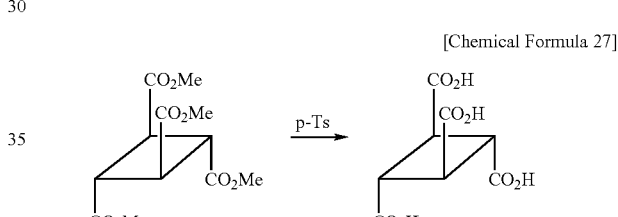

[Chemical Formula 27]

Synthesis started with charging a 500-mL four-neck flask of Pyrex (registered trade mark) glass with trans, trans, trans-tetramethyl-1,2,3,4-cyclobutanetetracarboxylate (30 g), p-toluenesulfonic acid monohydrate (p-TS for short) (0.9 g or 3 wt %), and formic acid (300 g). The reactants underwent refluxing with stirring at 100° C. for 4 hours.

The reaction was continued until the starting material was consumed, during which methyl formate (as a by-product) was distilled away with formic acid by $^1$H-NMR. The amount of methyl formate that was distilled away was 180 g. White crystals separated out as distillation proceeded.

The reaction was followed by cooling to room temperature and filtration for crystal collection. After washing with ethyl acetate and drying in vacuo, there was obtained 22.7 g of white crystals. Yields: 93.9%.

This product was identified, by MASS, $^1$H-NMR, and $^{13}$C-NMR, as trans, trans, trans-1,2,3,4-cyclobutanetetracarboxylic acid.

| MASS (FAB, m/e(%)): | 233 ([M + H]$^+$, 100) |
| --- | --- |
| $^1$H-NMR (DMSO-d$_6$, δ ppm): | 3.1351 (s, 4H), 12.7567 (s, 4H) |
| $^{13}$C-NMR (DMSO-d$_6$, δ ppm): | 40.3808, 172.8627 (each representing four carbons) |
| mp.: | 280.0° C. |

Example 9

Synthesis of 1,2,3,4-cyclobutanetetracarboxylic acid-1,3:2,4-dianhydride

[Chemical Formula 28]

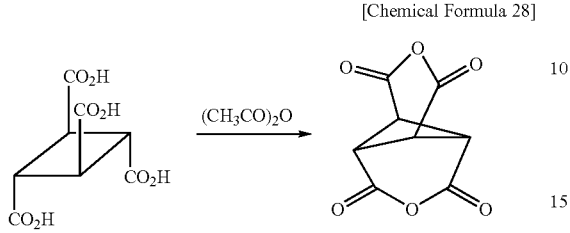

Synthesis started with charging a 100-mL four-neck flask of Pyrex (registered trade mark) glass with trans, trans, trans-1,2,3,4-cyclobutanetetracarboxylic acid (24 g), acetic anhydride (120 g or 5 times by weight), and toluene (120 g or 5 times by weight). The reactants were heated to 110° C. with stirring, and reaction was continued for 24 hours, during which white crystals separated out.

The reaction was followed by cooling to room temperature and filtration for crystal collection. After washing with ethyl acetate and drying in vacuo, there was obtained 15.1 g of white crystals. Yields: 74.5%.

This product was identified, by MASS, $^1$H-NMR, and $^{13}$C-NMR, as 1,2,3,4-cyclobutanetetracarboxylic acid-1,3:2,4-dianhydride.

| | |
|---|---|
| MASS (FAB, m/e(%)): | 197 ([M + H]$^+$, 100) |
| $^1$H-NMR (DMSO-$d_6$, δ ppm): | 4.2455 (s, 4H), 12.7714 (s, 4H) |
| $^{13}$C-NMR (DMSO-$d_6$, δ ppm): | 43.3971, 163.5640 (each representing four carbons) |
| mp.: | 258.0° C. |

Figure 2:
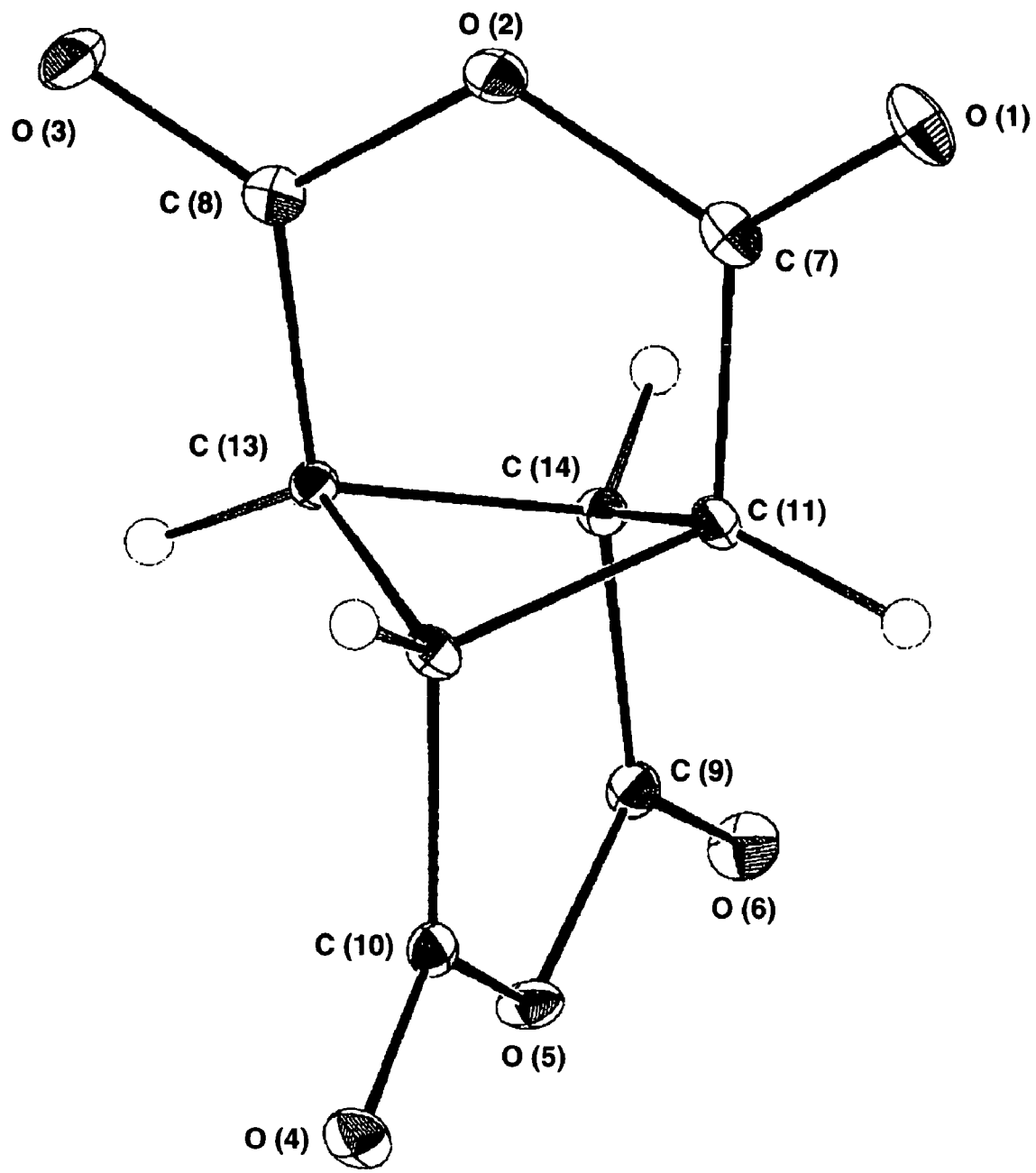
FIG. 2 is an X-ray diffraction chart of 1,2,3,4-cyclobutanetetracarboxylic acid-1,3:2,4-dianydride (in single-crystal form) which was obtained in Example 9.

The result of the X-ray analysis of the single crystal of 1,2,3,4-cyclobutanetetracarboxylic acid-1,3:2,4-dianhydride The X-ray analysis performed on the single crystal of 1,2,3,4-cyclobutanetetracarboxylic acid-1,3:2,4-dianhydride gave the following results and the molecular structure as shown in FIG. 2. (The specimen for X-ray analysis is the white crystal originally obtained by the above-mentioned reaction.)

| | |
|---|---|
| Molecular formula: | $C_8H_4O_6$ |
| Molecular weight: | 196.114 |
| Color and shape: | colorless and plate |
| Crystal system: | triclinic |
| Space group: | P-1 |
| Crystal form: | plane |
| Lattice constants: | a = 9.0610(10) Å |
| | b = 8.3480(10) Å |
| | c = 9.6980(10) Å |
| | α = 90.00° |
| | β = 90.00° |
| | γ = 90.00° |
| V = 733.57(14) Å$^3$ | |
| Z value = 4 | |
| Dx = 1.776 Mg/m$^3$ | |
| Mo K<α> radiation | |
| λ (MoKa) = 0.70926 Å, μ (MoKa) = 0.16 mm$^{-1}$ | |
| No. of measured reflections = 950 | |
| No. of observed reflections = 885 | |
| R(gt) = 0.034 | |
| wR(gt) = 0.075 | |
| Temp. = 130 K | |

Example 10

Synthesis of cis, trans, cis-tetramethyl-1,4-dimethyl-1,2,3,4-cyclobutanetetracarboxylate

[Chemical Formula 29]

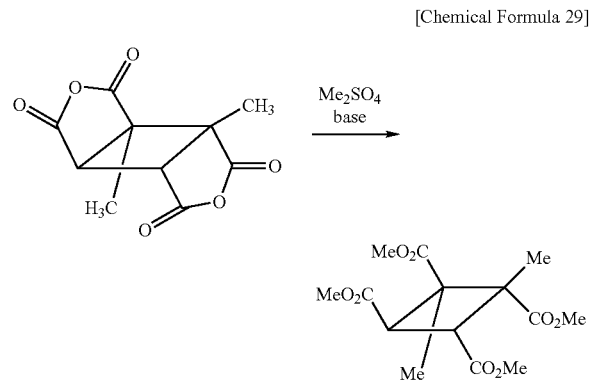

Synthesis started with charging a 200-mL four-neck flask of Pyrex (registered trade mark) glass with 1,4-dimethyl-1,2,3,4-cyclobutanetetracarboxylic acid-1,2:3,4-dianhydride (14.0 g or 58.08 mmol, 93% purity) and methanol (70 g, 5 times by weight). While heating in an oil bath at 60° C., the reactant was given dropwise diisopropylamine (18.6 g or 144 mmol) over 30 minutes with stirring.

With dimethyl sulfate (16.5 g or 131 mmol or 2.1 mol equivalent) added, the reactant underwent refluxing at 60° C. for 1.5 hours. The reaction was followed by concentration to dryness. Thus there was obtained a crude product (52.9 g). This crude product was given dropwise toluene (70 g) and 2% aqueous solution of hydrochloric acid (70 g) for dissolution. The resulting solution was separated, and the organic layer was washed with a 5% aqueous solution (42 g) and then with water (42 g). The washed organic layer was concentrated to give crude crystals (19.2 g). The crude crystals were given toluene (9.6 g) and heptane (38.4 g) for dissolution with heating. After cooling to 52° C., the resulting solution was given a seed crystal and allowed to stand at 20° C. for 30 minutes. The crystals which had separated out were filtered off and dried in vacuo. Thus there was obtained the desired product (14.9 g) in the form of white crystals which gave a single peak in gas chromatography (GC). Yields: 81.1%.

This product was identified, by $^1$H-NMR and $^{13}$C-NMR, as cis, trans, cis-tetramethyl-1,4-dimethyl-1,2,3,4-cyclobutanetetracarboxylate.

| | |
|---|---|
| $^1$H-NMR (DMSO-$d_6$, δ ppm): | 1.2664 (s, 6H), 3.3011 (s, 2H), 3.6189 (s, 6H), 3.6820 (s, 6H) |
| $^{13}$C-NMR (DMSO-$d_6$, δ ppm): | 19.9048 (2), 45.0419 (2), 51.5986 (2), 52.2327 (4), 170.9263 (2), 171.8576 (2) (parenthesized number denoting the carbon number) |
| mp.: | 86.1° C. |

Example 11

Synthesis of trans, trans, trans-tetramethyl-1,2-dimethyl-1,2,3,4-cyclobutanetetracarboxylate

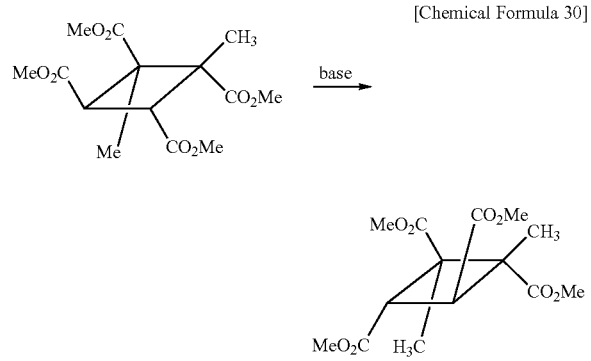

[Chemical Formula 30]

Synthesis started with charging a 100-mL four-neck flask of Pyrex (registered trade mark) glass with cis, trans, cis-tetramethyl-1,4-dimethyl-1,2,3,4-cyclobutanetetracarboxylate (26.7 g or 84.4 mmol) and tetrahydrofuran (THF) (134 g, 5 times by weight). While stirring at 5° C., the reactant was given potassium t-butoxide of 95% purity (0.474 g or 4.74 mmol or 5 mol %) and then kept stirring at 5° C. for 1 hour.

With the solvent removed by evaporation, the residues were given toluene (134 g or 5 times by weight) and the resulting solution was concentrated to remove toluene. The residues were further given toluene (134 g or 5 times by weight) and water (134 g or 5 times by weight) for dissolution. The resulting solution was separated and the organic layer was concentrated to give crude crystals (26.8 g). The crude crystals were given toluene (26.7 g) and heptane (48 g) for dissolution with heating. After cooling to 35 to 40° C., the solution was given a seed crystal and cooled to 20 to 25° C. with stirring for 30 minutes. The crystals which had separated out were filtered off and dried in vacuo. Thus there was obtained the desired product (16.7 g) in the form of white crystals which gave a single peak in gas chromatography (GC). Yields: 62.5%. Upon concentration, the filtrate gave 8.6 g of crystals.

This product was identified, by $^1$H-NMR and $^{13}$C-NMR, as trans, trans, trans-tetramethyl-1,2-dimethyl-1,2,3,4-cyclobutanetetracarboxylate.

| | |
|---|---|
| $^1$H-NMR (DMSO-$d_6$, δ ppm): | 1.1248 (s, 6H), 3.6436 (s, 6H), 3.7169 (s, 6H), 3.8995 (s, 2H) |
| $^{13}$C-NMR (DMSO-$d_6$, δ ppm): | 15.3129 (2), 39.7827 (2), 49.2593 (2), 51.9986 (2), 52.4945 (2), 170.2656 (2), 171.3643 (2) (parenthesized number denoting the carbon number) |
| mp.: | 82.4° C. |

Example 12

Synthesis of trans, trans, trans-1,2-dimethyl-1,2,3,4-cyclobutanetetracarboxylic acid

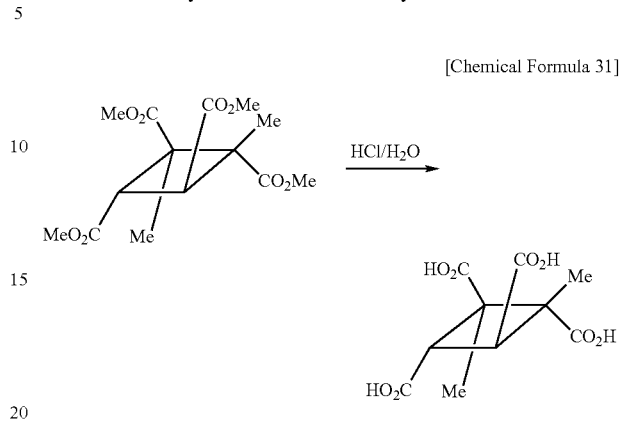

[Chemical Formula 31]

Synthesis started with charging a 500-mL four-neck flask of Pyrex (registered trade mark) glass with trans, trans, trans-tetramethyl-1,2-dimethyl-1,2,3,4-cyclobutanetetracarboxylate (15 g or 47.4 mmol) and 2N hydrochloric acid (150 g or 274 mmol or 5.78 mol equivalent). With the temperature raised to 100° C. with stirring, reaction continued for 9 hours under refluxing to remove 7 g each of alcohol (as a by-product) at intervals of 30 minutes. Upon concentration to dryness, the reaction solution gave 16.4 g of residue.

This residue was dehydrated by azeotropic distillation with toluene (75 g) to give 11.6 g of solid product. This solid product was crystallized from its solution in ethyl acetate (45 g) after reflux for 30 minutes and stirring at 20 to 25° C. for 30 minutes. The resulting crystals were filtered out, washed with toluene and then with ethyl acetate, and finally dried in vacuo. Thus there was obtained a product (11.1 g) in the form of white crystals. Yields: 89.7%.

This product was identified, by $^1$H-NMR and $^{13}$C-NMR, as trans, trans, trans-1,2-dimethyl-1,2,3,4-cyclobutanetetracarboxylic acid.

| | |
|---|---|
| $^1$H-NMR (DMSO-$d_6$, δ ppm): | 1.1833 (s, 6H), 3.7137 (s, 2H), 12.6874 (s, 4H) |
| $^{13}$C-NMR (DMSO-$d_6$, δ ppm): | 15.5255 (2), 39.8732 (2), 40.0030 (2), 48.4648 (2), 172.2102 (2), 173.0419 (2) (parenthesized number denoting the carbon number) |
| mp.: | 280.4° C. |

Example 13

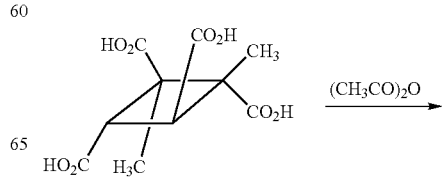

[Chemical Formula 32]

-continued

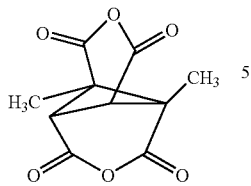

Synthesis started with charging a 200-mL four-neck flask of Pyrex (registered trade mark) glass with trans, trans, trans-1,2-dimethyl-1,2,3,4-cyclobutanetetracarboxylic acid (14.6 g), acetic anhydride (43.8 g or 3 times by weight), and toluene (43.8 g or 3 times by weight). The reactants were heated to 107° C. with stirring and were refluxed for 5 hours, during which white crystals slightly separated out after 3 hours.

The reaction was followed by cooling to 20° C. and filtration for crystal collection. After washing with toluene and drying in vacuo below 40° C., there was obtained 10.9 g of white crystals. Yields: 86.3%.

This product was identified, by MASS, $^1$H-NMR, and $^{13}$C-NMR, as 1,2-dimethyl-1,2,3,4-cyclobutanetetracarboxylic acid-1,3:2,4-dianhydride.

| | |
|---|---|
| MASS (FAB, m/e(%)): | 225.08 ([M + H]$^+$, 18), 79.06 (100) |
| $^1$H-NMR (DMSO-d$_6$, δ ppm): | 1.3162 (s, 6H), 4.4171 (s, 2H) |
| $^{13}$C-NMR (DMSO-d$_6$, δ ppm): | 12.6168 (4), 45.8766 (4), 52.7284 (2), 162.9991 (2), 165.1050 (2) (parenthesized number denoting the carbon number) |
| mp.: | 234.1° C. |

Figure 3:
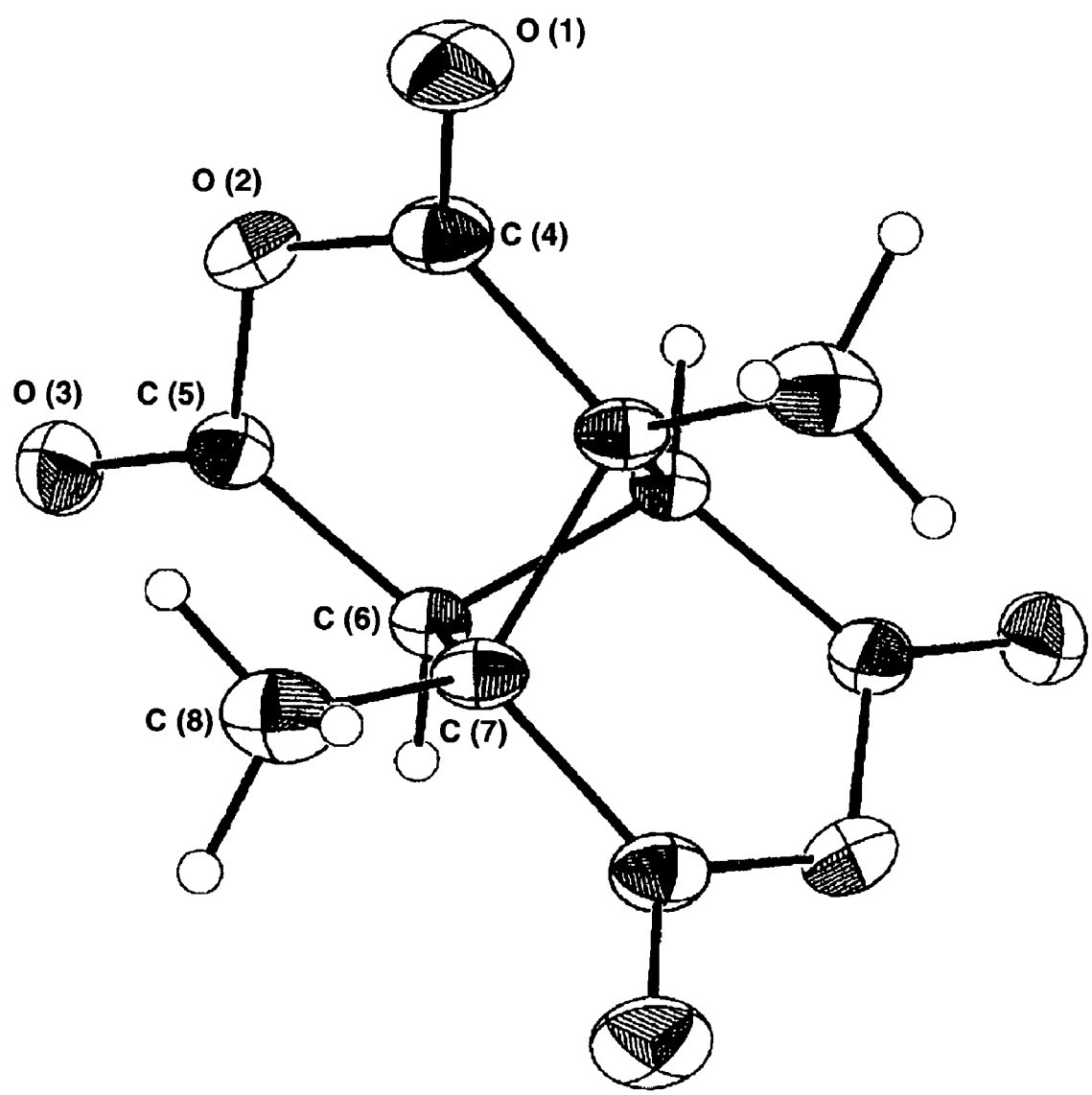
FIG. 3 is an X-ray diffraction chart of 1,2-dimethyl-1,2,3,4-cyclobutanetetracarboxylic acid-1,3:2,4-dianydride (in single-crystal form) which was obtained in Example 13.

The result of the X-ray analysis of the single crystal of 1,2-dimethyl-1,2,3,4-cyclobutanetetracarboxylic acid-1,3:2,4-dianhydride The X-ray analysis performed on the single crystal of 1,2-dimethyl-1,2,3,4-cyclobutanetetracarboxylic acid-1,3:2,4-dianhydride gave the following results and the molecular structure as shown in FIG. 3. (The specimen for X-ray analysis is a colorless columnar single crystal which crystallized out from a solution of the white crystals (originating from the above-mentioned reaction) in a mixture of acetic anhydride and toluene at 70° C. after slow cooling to room temperature.

| | |
|---|---|
| Molecular formula: | C$_{10}$H$_8$O$_6$ |
| Molecular weight: | 224.168 |
| Color and shape: | colorless and columnar |
| Crystal system: | orthorhombic |
| Space group: | Pbcn |
| Lattice constants: | a = 9.902(1) Å |
| | b = 9.000(1) Å |
| | c = 11.096(1) Å |
| | α = 90.00° |
| | β = 90.00° |
| | γ = 90.00° |
| V = 988.9(2) Å$^3$ | |
| Z value = 4 | |
| Dx = 1.506 Mg/m$^3$ | |
| Mo K<α> radiation | |
| λ (MoKa) = 0.70926 Å, μ (MoKa) = 0.13 mm$^{-1}$ | |
| No. of measured reflections = 1282 | |
| No. of observed reflections = 1081 | |
| R(gt) = 0.067 | |
| wR(gt) = 0.145 | |
| Temp. = 298 K | |

The invention claimed is:

1. A process which comprises the steps of:
reacting 1,2,3,4-cyclobutanetetracarboxylic acid-1,2:3,4-dianhydride represented by formula [1]

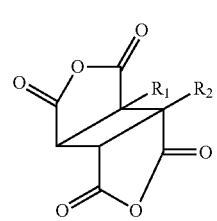

[1]

wherein R$^1$ and R$^2$ each independently denotes a hydrogen atom, a halogen atom, a C$_{1-10}$ alkyl group, a C$_{1-10}$ halogenated alkyl group, a C$_{3-8}$ cycloalkyl group, a phenyl group, or a cyano group with a dialkyl sulfate represented by the formula [7]

$$R^3{}_2SO_4 \qquad [7]$$

wherein R$^3$ denotes a C$_{1-10}$ alkyl group in the presence of a base catalyst, thereby producing cis, trans, cis-1,2,3,4-cyclobutane tetracarboxylic acid tetraester represented by the formula [3]

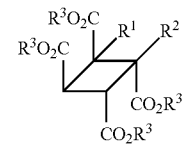

[3]

wherein R$^1$, R$^2$, and R$^3$ are as defined above;
converting the compound of the formula [3] into the compound of the formula [4]

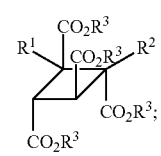

[4]

converting the compound of the formula [4] into the compound of the formula [5]

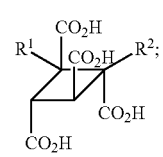

[5]

and converting the compound of the formula [5] into the compound of the formula [6]

[6]

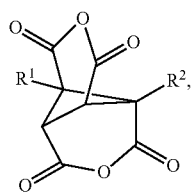

thereby producing 1,2,3,4-cyclobutanetetracarboxylic acid-1,3:2,4-dianhydride.

2. The process of claim 1, wherein $R^1$ and $R^2$ are independently $C_{1-10}$ alkyl groups.

3. The process of claim 1, wherein $R^1$ and $R^2$ are methyl groups.

4. The process of claim 1, wherein the dialkyl sulfate represented by the formula [7] is dimethyl sulfate.

5. The process of claim 1, wherein the base catalyst is an aliphatic amine.

* * * * *